(12) United States Patent
Couillard et al.

(10) Patent No.: US 6,244,838 B1
(45) Date of Patent: Jun. 12, 2001

(54) FLUID PUMPING PROCESS AND SYSTEM USING A PUMP WITH A CONSTANT INTAKE OR DELIVERY RATE

(75) Inventors: François Couillard, 56038, Vannes Cedex; André Renot, rue François Plasson, both of (FR)

(73) Assignees: Institut du Francais Petrole, Rueil Malmaison Cedex; Francois Couillard, Vannes Cedex, both of (FR)

( * ) Notice: Subject to any disclaimer, the term of this patent is extended or adjusted under 35 U.S.C. 154(b) by 0 days.

(21) Appl. No.: 09/392,624

(22) Filed: Sep. 9, 1999

(30) Foreign Application Priority Data

Sep. 9, 1998 (FR) .................................................. 98 11284

(51) Int. Cl.[7] ............................. F04B 23/04; F04B 41/06
(52) U.S. Cl. ................................................. 417/426; 417/5
(58) Field of Search ................................. 417/5, 416, 426

(56) References Cited

U.S. PATENT DOCUMENTS

| | | | |
|---|---|---|---|
| 4,233,156 | | 11/1980 | Tsukada et al. ..................... 210/101 |
| 4,278,205 | * | 7/1981 | Binoche ................................ 417/214 |
| 4,321,014 | * | 3/1982 | Eburn et al. ............................. 417/5 |
| 4,643,649 | * | 2/1987 | Schmid ................................... 417/45 |
| 5,406,784 | * | 4/1995 | Vertens et al. ...................... 60/39.03 |
| 5,641,270 | * | 6/1997 | Sgourakes et al. ................. 417/44.2 |
| 5,719,302 | | 2/1998 | Perrut et al. .......................... 554/191 |
| 5,755,561 | * | 5/1998 | Couillard et al. .................... 417/246 |
| 5,993,174 | * | 11/1999 | Konishi et al. ..................... 417/413.1 |

* cited by examiner

Primary Examiner—Timothy S. Thorpe
Assistant Examiner—Michael K. Gray
(74) Attorney, Agent, or Firm—Antonelli, Terry, Stout & Kraus, LLP

(57) ABSTRACT

The invention is a system and process for pumping fluids in lines, comprising using, on the lines, a pump with at least two alternating fluid pumping units. Each pumping unit (PU1, PU2) comprises a cylinder (2) and a piston (1) alternately displaceable in the cylinder under the action of a power source (M), under the control of a control device (PC), with, for both pistons, imposed displacement functions (f(t), g(t)) suitably phase-shifted in relation to one another so as to obtain a first operating mode corresponding to substantially constant delivery rate. This pump is operated in the same circuit according to the complementary second operating mode corresponding to a substantially constant intake rate by inversion of the direction of displacement of the pistons so as to apply to the pistons displacement functions (−f(t), −g(t)) symmetrical to those corresponding to the first operating mode. The selection of substantially constant delivery or intake rate is dependent upon the circuits to which the invention is applied. The process can be applied for example in the field of chromatography.

10 Claims, 3 Drawing Sheets

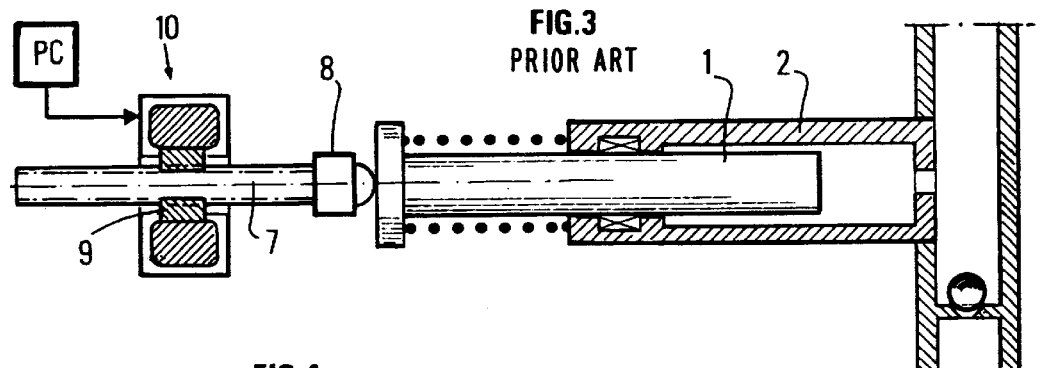
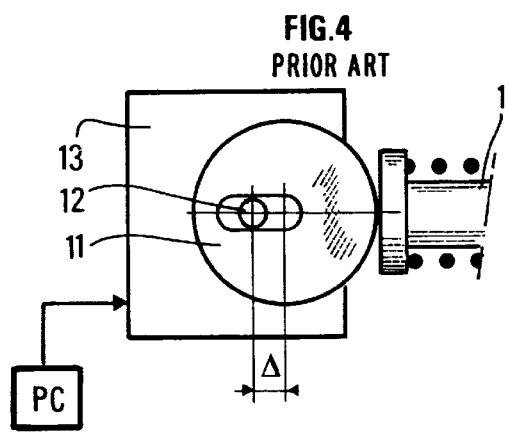
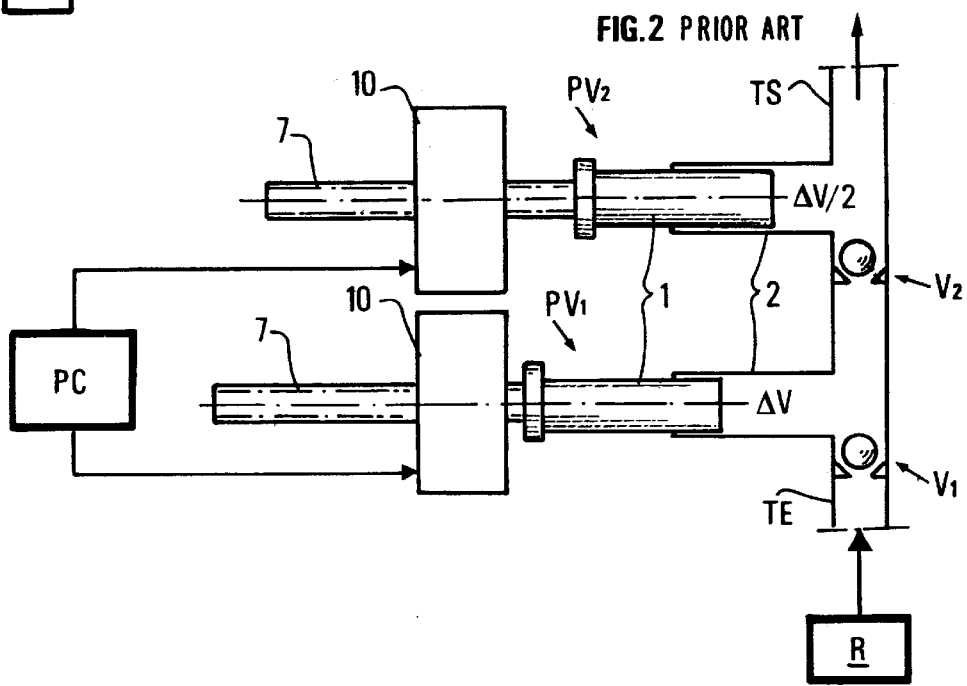

US 6,244,838 B1

FLUID PUMPING PROCESS AND SYSTEM USING A PUMP WITH A CONSTANT INTAKE OR DELIVERY RATE

BACKGROUND OF THE INVENTION

1. Field of the Invention

The present invention relates to a reversible fluid pump that can work with a constant intake or delivery rate and to a hydraulic system using such a pump.

It more particularly relates to a reversible pump with two alternating pumping elements interconnected in series or in parallel, that can work with a constant intake or delivery rate in a fluid circulation system such as those that can be found in various industry types. The pump according to the invention finds applications notably in chromatography systems.

2. Description of the Prior Art

Various pump types can be used for circulating liquid mixtures such as, for example, alternating pumps comprising generally two alternating linear pumping units arranged in parallel.

According to the embodiment of FIG. 1, each of the two units arranged in parallel comprises a piston, sliding in a cylinder 2 communicating, by means of a one-way valve 4 opening during the intake phase, with an inlet line 3 coming from a first tee T1 delivering a liquid L. The two units PU1, PU2 also communicate, through an outlet line 5 and by means of valves 6 opening during the delivery phase, with a second delivery tee T2. Phase shift of units PU1, PU2 is controlled by power sources M under the control of a control device PC so that the intake phase of one substantially corresponds to the delivery phase of the other.

Various types of power sources M can be used.

The stroke depth of each rod 1 in its cylinder 2 can for example be provided (FIG. 3) through the translation of a screw 7 resting on the head of piston 1 by means of a ball thrust 8. The screw translation comprises for example a nut 9 threaded to screw 7, that is for example housed in the hollow rotor of a stationary electric motor 10 and driven in rotation thereby. The direction of translation of the screw is changed by inverting the direction of rotation of the motor every pumping half cycle.

According to a second embodiment (FIG. 4), the stroke depth of piston 1 in body 2 is provided by the rotation of a cam 11 resting against the head of piston 1, whose pin 12 is driven in rotation by a motor 13. The stroke depth of piston 1 in the inner cavity of body 2 is obtained by changing the offset Δ of the cam on the axis thereof. In either case, motor 13 is driven by a control computer PC.

The speed of each piston 1 decreases at the end of its stroke, and consequently so does the flow delivered thereby. If the global rate of delivery of units PU1, PU2 (FIG. 1) has to be substantially constant, the sum of the speeds of the two pistons must remain constant and the delivery phase of unit PU2 for example must therefore start before first unit PU1 has totally finished. During the relatively short fraction of each cycle where the two units deliver at the same time, the intake rate is zero, which results in a pulsed intake rate of the pump.

In a pump with two units PU1, PU2 arranged in series (FIG. 2), unit PU1 draws fluid out of a fluid tank R through a line TE on which a first nonreturn valve V1 is interposed. It drives it through a second nonreturn valve V2, towards unit PU2. The latter drives the pumped fluid through a line TS to the pump outlet. When piston 1 of unit PU1 is in the delivery phase and drives a volume ΔV towards unit PU2 downstream, piston 1 of unit PU2 is moved back so that it draws a volume $\Delta V_s = \Delta V/2$ taken from the volume delivered by first unit PU1. The volume expelled through line TS is thus equal to ΔV/2. When piston 1 of the same unit PU1 goes into the intake phase and valve V2 closes, piston 1 of second unit PU2 goes into the delivery phase and expels the previously drawn volume $\Delta V_s = \Delta V/2$ towards line TS. The flow expelled through line TS is constant provided that the motion laws applied to both pistons are so selected that the sum of their respective speeds is permanently constant. An example of a pump of this type is described in U.S. Pat. No. 5,755,561 filed by the assignee.

SUMMARY OF THE INVENTION

The present invention relates to a process for pumping a fluid in a circuit, comprising using in the circuit a pump with at least two alternating fluid pumping units comprising each a cylinder and a piston displaceable in the cylinder, with imposed displacement functions for the pistons, suitably phase-shifted in relation to one another so as to obtain a first operating mode corresponding either to a substantially constant intake rate or to a substantially constant delivery rate.

The pumping process is characterized in that the pump is operated in the same circuit according to a second operating mode complementary to the first mode, by inverting the direction of displacement of the pistons so as to apply thereto displacement functions symmetrical to those corresponding to the first mode.

The system for pumping fluids in lines according to the invention comprises at least one pump provided with at least two alternating fluid pumping units comprising each a cylinder and a piston displaceable in the cylinder. It comprises a drive for alternately displacing the two pistons, suited to apply respectively to the pistons of the pumping units displacement functions (f(t), g(t)) as a function of time t, suitably phase-shifted in relation to one another, in order to obtain a first operating mode of the pump with a substantially constant intake or delivery rate.

The pumping system comprises an inverting system acting on the drive for displacing the two pistons in order to apply displacement functions (−f(t), −g(t)) symmetrical to the previous ones and to obtain for the pump a second operating mode complementary to the first mode, with a substantially constant intake or delivery rate.

According to an embodiment, the system for displacing each piston comprises a screw alternately displaced parallel to its axis, by a driving motor, and a control device for changing alternately the direction of rotation of the driving motor in accordance with the operating mode selected.

According to another embodiment, the system for displacing each piston comprises shaped cams driven in rotation by a single motor, and a control device for controlling the motor according to the operating mode selected.

The pumping system can comprise several pumps installed for example on various lines of a set of lines and a control device suited to select, for each pump, the first or the second operating mode so as to comply with determined conditions of circulation in the set of lines.

According to an embodiment, the pumping system comprises several pumps in a circuit and on fluid injection and/or extraction branch lines, the control device being suited to control the motors of the various pumps so that the sum of the volumes of fluid injected at a constant rate according to the second operating mode is substantially equal to the sum of the volumes of fluid extracted at a constant rate according to the first operating mode.

BRIEF DESCRIPTION OF THE DRAWINGS

Other features and advantages of the process and of the system according to the invention will be clear from reading the description hereafter of non limitative examples, with reference to the accompanying drawings wherein.

DETAILED DESCRIPTION OF THE PREFERRED EMBODIMENTS

Figure 1:
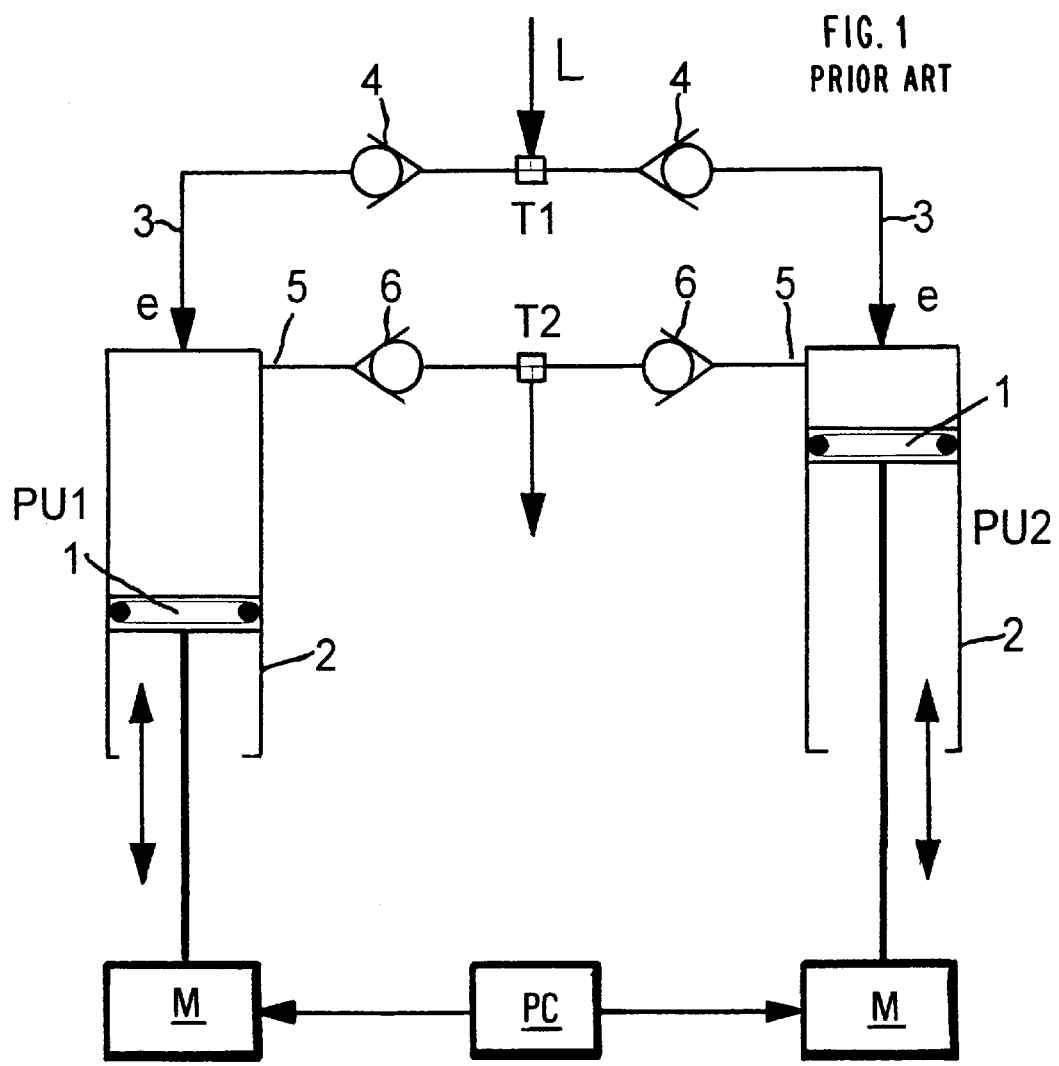
FIG. 1 diagrammatically shows a first type of prior art alternating pumping with two units in parallel, FIG. 2 diagrammatically shows a second type of prior art alternating pumping with two units in parallel, FIG. 3 diagrammatically shows a first prior art mode of driving a pump piston by means of a screw, FIG. 4 diagrammatically shows a second prior art mode of driving a pump piston by means of a cam.
Figure 5:
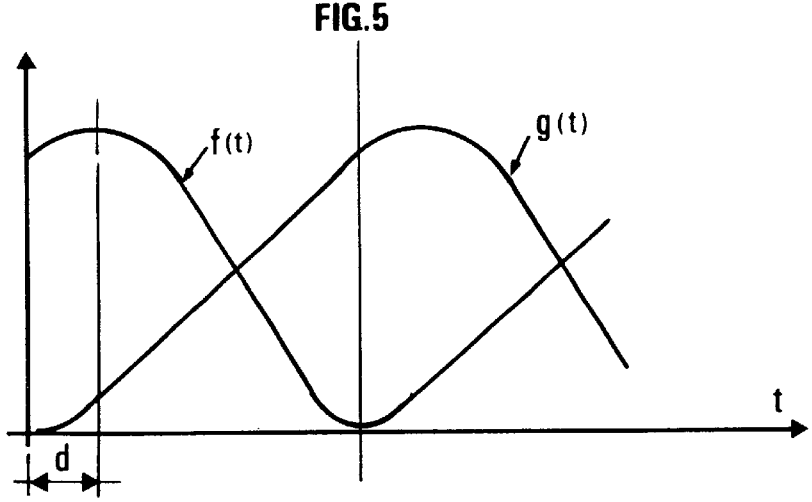
FIG. 5 shows an example of respective displacement laws for the pistons of the pumping units of FIG. 1, in accordance with the invention suitably phase-shifted in relation to one another so as to obtain a constant delivery rate, and FIG. 6 diagrammatically shows a loop such as those used in chromatography, where the pumps according to the invention can be used to precisely comply with flow rate constraints.

An example of the invention is a pump such as that of FIG. 1, where the two pumping units PU1 PU2 arranged in parallel are actuated by the piston drive of FIGS. 3 or 4, with respective displacement laws $f(t)$ and $g(t)$ as shown in FIG. 5. The two functions $f(t)$ and $g(t)$ are phase-shifted in relation to one another so that the delivery phases are not totally separate in time. A constant delivery rate is thus obtained if the sum of the derivatives $f'(t)$ and $g'(t)$ of these two functions remains constant. During the time interval d where the two pistons move in the same direction, the intake rate is of course zero.

The pumping process according to the invention essentially controls the rotation of each motor driving the cams or the screws of the pumps (FIGS. 1 or 2) so as to apply to the pistons displacement functions $f(t)$ and $g(t)$ in one direction and symmetrical displacements $-f(t)$ and $-g(t)$ in the opposite direction, which has the effect of producing, in the first direction, a constant delivery rate for example and, in the opposite direction, a constant intake rate for the same pump, without changing connections on the line on which the pump is placed. In the first case, it is the intake rate that will show fluctuations. In the other direction, it is the delivery rate that will show fluctuations.

Using such a pump is advantageous in all the fields of application where only one of the criteria: constant intake rate or constant delivery rate is important.

This is the case in hydraulic systems where determined fluid circulation conditions are imposed: circulation of various fluids with set flow rate values for various flow rates at one or more points, for the smooth course of a process in progress.

Figure 6:
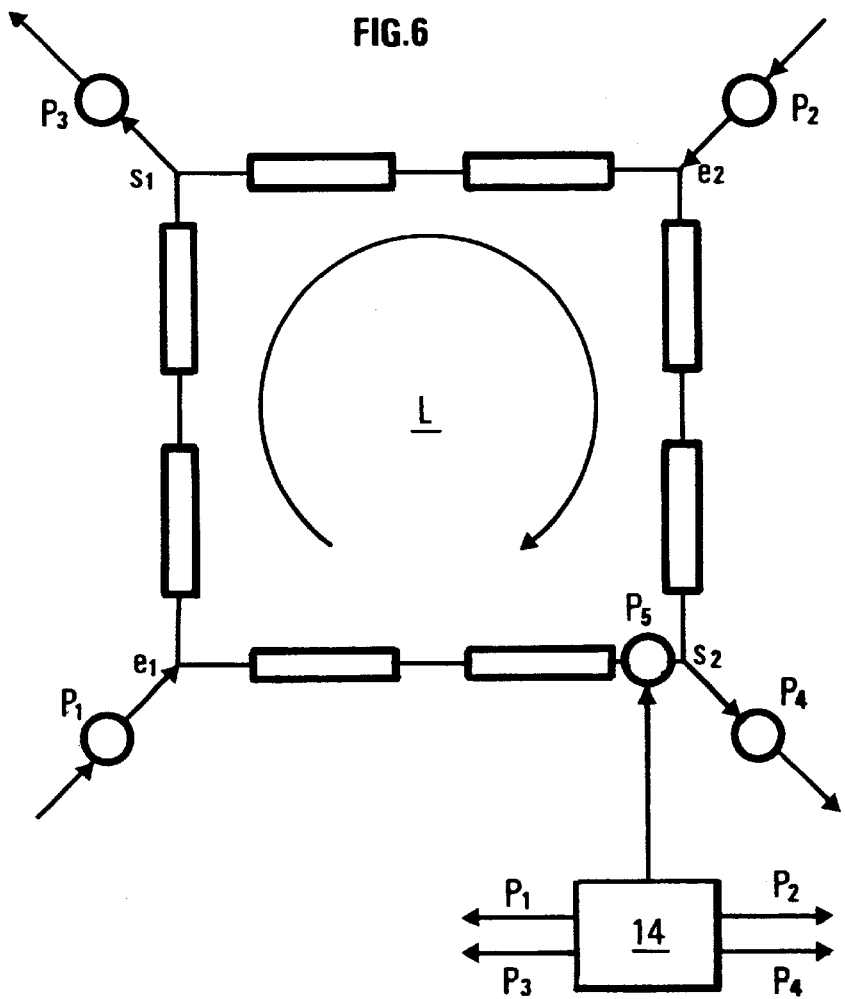

Simulated moving bed type separation systems as described in U.S. Pat. No. 5,114,590 or U.S. Pat. No. 5,902,486 can be taken as an example. As shown in FIG. 6, such a system comprises a set of columns or column sections interconnected in series, forming a closed loop L. Along this loop are distributed injection points e1, e2 for a mixture to be separated and a solvent or desorbent, and fluid extraction points s1, s2: extract and raffinate, delimiting several zones. The fluids are injected at injection points e1, e2 by means of pumps P1, P2. The fluids are extracted at extraction points s1, s2 respectively by pumps P3, P4. Control device 14 selects for each pump a first or second operating mode so as to comply with determined conditions of circulation in the set of lines. Control device 14 controls the motors of the various pumps so that the sum of the volumes of fluid which are injected at a constant rate according to the second operating mode is substantially equal to the sum of the volumes of fluid which are extracted at a constant rate according to the first operating mode.

In such a system, it is important that injections and extractions are carried out at non-pulsed constant flow rates. The pumps described above can be used while selecting for each one the suitable operating mode at the point where it is connected.

Thus, for the branch lines arriving at e1, e2, the mode allowing a non-pulsed constant delivery rate is selected for pumps P1, P2, possible pulsations at the inlet of these two pumps having no effect on the operation of the loop. On the branch lines from points s1, s2, an operating mode where, conversely, it is the intake rate that is constant and non-pulsed is selected for pumps P3, P4. Possible pulsations at the outlets thereof have no effect on the operation of the loop.

A circulation pump P5 having both a constant intake and delivery rate is installed on the loop. A pump with three pumping units such as that described in French patent FR-2 768 189 of the assignee can be used for example.

What is claimed is:

1. A process for pumping fluids in lines, using at least one pumping system having at least two alternating fluid pumping units each with a cylinder and a piston displaceable in the cylinder, and a drive for applying respectively to the pistons of the at least two pumping units alternative displacements phase-shifted in relation to one another, comprising:

applying to the drive first displacement functions ($f(t)$, $g(t)$) as a function of time t, which provide a first operating mode of the at least two alternating fluid pumping units with a substantially constant delivery rate; and applying to the drive second displacement functions ($-f(t)$, $-g(t)$), respectively symmetrical of the first displacement functions, which provide a second operating mode of the at least two alternating fluid pumping units with a substantially constant intake rate.

2. A system for pumping fluids in lines, comprising:

at least one pumping system having at least two alternating fluid pumping units each with a cylinder and a piston displaceable in the cylinder; and a drive which applies respectively to the pistons of the at least two pumping units alternative displacement functions ($f(t)$, $g(t)$) as a function of time t, phase-shifted in relation to one another and producing a first operating mode of the at least one pumping system with a substantially constant delivery rate, and which applies respectively to the pistons of the at least two pumping units second displacement functions ($-f(t)$, $+g(t)$), symmetrical to the first displacement functions, and producing a second, complementary operating mode of the at least one pumping system with a substantially constant intake rate.

3. A system as claimed in claim 2, wherein:

the drive includes a screw, a driving motor for displacing the screw, and a control device for alternately changing a direction of rotation of the driving motor in accordance with the selected first or second operating mode.

4. A system as claimed in claim 2, wherein:

the drive includes cams, a motor for driving the cams in rotation and a control device for alternately changing a direction of rotation of the driving motor in accordance with the selected first or second operating mode.

5. A system as claimed in claim 2, comprising:

pumping systems installed on the lines and a control which selects, for each pumping system, the first or the second operating mode to comply with determined conditions of circulation in the installed lines.

6. A system as claimed in claim 3, comprising:

pumping systems installed on the lines and a control which selects, for each pumping system, the first or the second operating mode to comply with determined conditions of circulation in the installed lines.

7. A system as claimed in claim 4, comprising:

pumping systems installed on the lines and a control which selects, for each pumping system, the first or the second operating mode to comply with determined conditions of circulation in the installed lines.

8. A system as claimed in claim 5, comprising:

pumping systems in a circuit provided with fluid injection and extraction branch lines, and a control device for controlling the drive of the pumping systems so that a sum of volumes of fluid injected at a substantially constant rate according to the second operating mode is substantially equal to the sum of the volumes of fluid extracted at a substantially constant rate according to the first operating mode.

9. A system as claimed in claim 6, comprising:

pumping systems in a circuit provided with fluid injection and extraction branch lines, and a control device for controlling the drive of the pumping systems so that a sum of volumes of fluid injected at a substantially constant rate according to the second operating mode is substantially equal to the sum of the volumes of fluid extracted at a substantially constant rate according to the first operating mode.

10. A system as claimed in claim 7, comprising:

pumping systems in a circuit provided with fluid injection and extraction branch lines, and a control device for controlling the drive of the pumping systems so that a sum of volumes of fluid injected at a substantially constant rate according to the second operating mode is substantially equal to the sum of the volumes of fluid extracted at a substantially constant rate according to the first operating mode.

* * * * *